United States Patent [19]

Campolmi et al.

[11] 4,390,733
[45] Jun. 28, 1983

[54] PROCESS FOR PREPARING THE MONO-METHALLYL ETHER OF PYROCATECHIN

[75] Inventors: Stefano Campolmi, Novara; Vittorio Carletti, Meda; Marcello Marchi, Novara, all of Italy

[73] Assignee: Montedison S.p.A., Milan, Italy

[21] Appl. No.: 263,598

[22] Filed: May 14, 1981

[30] Foreign Application Priority Data

May 16, 1980 [IT] Italy .................. 22129 A/80

[51] Int. Cl.³ .................................. C07C 41/16
[52] U.S. Cl. ............................ 568/652; 568/651
[58] Field of Search ...................... 568/651, 452

[56] References Cited

U.S. PATENT DOCUMENTS 4,250,333 2/1981 Rakoutz .................. 568/652

OTHER PUBLICATIONS

Laskina et al., Chem. Abs., vol. 61 (1964) 11919(b)–(d).
The Condensed Chemical Dictionary, 8th Ed. (1971), 294–295.

*Primary Examiner*—Bernard Helfin

[57] ABSTRACT

The mono-methallyl ether of pyrocatechin of formula (I):

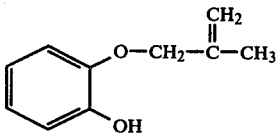

is prepared by reacting pyrocatechin of formula (II):

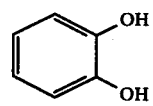

with a methallyl halide of formula (III):

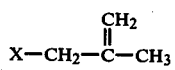

in a homogeneous dissolving medium, e.g., alcohols, aliphatic polyalcohols and monoethers thereof, or water, in the presence of an organic or inorganic base.

The mono-methallyl ether of pyrocatechin is used as an intermediate for organic syntheses and, in particular for synthesizing the product of formula (IV);

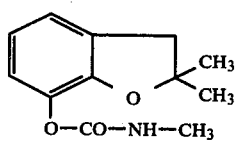

which is marketed under the tradename "Carbofuran" and is a compound which is the active principle in soil insecticides of different overall compositions which are available on the market.

17 Claims, No Drawings

PROCESS FOR PREPARING THE MONO-METHALLYL ETHER OF PYROCATECHIN

BACKGROUND OF THE INVENTION

Methods are known for preparing compound (I) by selective mono-etherification of pyrocatechin (II) with methallyl halides (III) in the presence of inorganic bases and in aprotic solvents such as dimethylsulphoxide (DMSO) and N-methyl-2-pyrrolidone.

However, the aprotic solvents are expensive and of such relatively low stability that recovery thereof requires particular care and high operating efficiency, which adversely affects both the operation and cost.

On the other hand, the recovery of unreacted pyrocatechin from the resulting reaction mixtures presents some difficulties which entail high losses of pyrocatechin along with a high cost of the operation itself and render it desirable to aim at the highest possible conversion obtainable by employing the aforesaid sophisticated, special solvents.

Nevertheless, operating under conditions directed to attaining very high conversion values involves, in some cases, a practically unavoidable formation of by-products, such as di-methallyl-ether of pyrocatechin of formula (V):

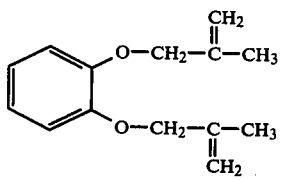

as well as of alkylation products on the aromatic ring. In these conditions it is therefore absolutely necessary to reduce as much as possible the formation of such by-products in order to prevent the economic and operating advantages expected from the high conversions from being partially jeopardized.

THE PRESENT INVENTION

It is an object of the present invention to provide a method of preparing the mono-methallyl ether of pyrocatechin free from the drawbacks of the prior art methods. A particular object of the invention is to provide a process employing on one hand less expensive solvents than those of the prior art, and leading, on the other hand, to high conversions and selectivities in the product to be obtained.

These and other objects are achieved by the invention in accordance with which it has surprisingly been found that the use, as a reaction medium, of particular hydroxylated solvents, also homogeneously mixed with one another, in the presence of organic or inorganic bases, leads to high conversions referred to pyrocatechin, maintaining acceptable selectivity values in the mono-methallyl ether of pyrocatechin of formula (I), while the formation of by-products is maintained at correspondingly allowable values.

To the best of our knowledge, the hydroxylated solvents used in practicing the present invention have never been utilized in the etherification of pyrocatechin with methallyl halides and have not led to the obtainment of a product with commercial scale yields and selectivities.

The process conducted according to this invention can be considered, by consequence, as representing a surprising overcoming of a prejudice existing in the prior art in general, according to which selective alkylation reactions, like the one utilized in the present invention, could not be consistent with the use of hydroxylated solvents, at least as regards the high conversion values associated with acceptable selectivity values.

This situation tended to dissuade those skilled in the art from further researches in the field or from expecting the surprisingly better results achieved by the present process.

The foregoing and still other objects which will more clearly appear to those skilled in the art from the following description, are achieved, according to the present invention, by a process for selectively preparing the mono-methallyl ether of pyrocatechin of formula (I), characterized in that the pyrocatechin of formula (II) is reacted with a methallyl halide of formula (III), preferably the chloride, in a homogeneous solvent selected from the low molecular weight saturated and unsaturated aliphatic alcohols, the polyalcohols and the monoethers thereof, water and mixtures thereof, at temperatures in the range of from about 30° to about 120° C., in the presence of an organic or inorganic base. The reaction can be schematically represented by the following equation:

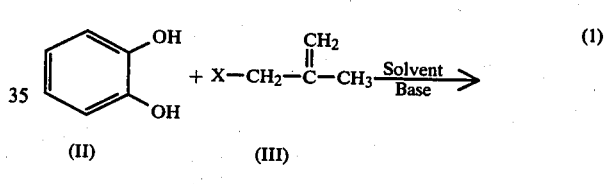

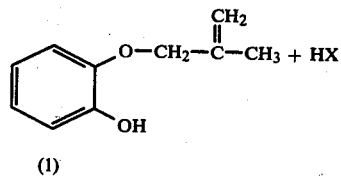

X being halogen.

The reaction is conducted in a homogeneous dissolving medium consisting of one or more of the hydroxylated compounds defined above, including mixtures thereof.

The hydroxylated compounds comprised in the present invention are water, the saturated and unsaturated alcohols having up to 5 carbon atoms in the molecule, polyalcohols and monoethers thereof, the last having the formula (VI)

$$RO[(CH_2)_nO]_mH \quad (VI)$$

wherein R is an alkyl having up to 10 carbon atoms and m and n are integers ranging from 1 to 10.

Presently preferred alcohols are the linear and branched saturated aliphatic alcohols $C_1$-$C_5$, in particular ethyl alcohol, the polyalcohols, such as ethylene glycol, the linear and branched unsaturated aliphatic alcohols $C_1$-$C_5$, such as, for example, allyl alcohol and of the monoethers of formula (VI), methyl- and ethyl "Cellosolve".

The use of aqueous mixtures of said (poly)alcohols is of particular interest in the economic and industrial respects.

The inorganic bases can be selected from among the oxides, hydroxides, carbonates, bicarbonates and acid phosphates of the alkaline metals, preferably from the sodium and potassium carbonates and bicarbonates. The organic bases can be selected from among the tertiary amines N(R')$_3$ in which (R')$_3$ is a homogeneous or heterogeneous hydrocarbyl group, such as triethylamine, and tetramethylguanidine.

The weight ratio between pyrocatechin (II) and the dissolving medium varies from 1:5 to 1:50 approximately, preferably from 1:10 to 1:30 approximately. The molar ratio between pyrocatechin (II) and the base varies from 1:0.5 to 1:3 approximately, preferably from 1:1 to 1:1.5 approximately.

The molar ratio between pyrocatechin (II) and methallyl halide (III) varies from 1:0.5 to 1:3 approximately, preferably from 1:1 to 1:1.5 approximately.

The reaction times range approximately from 1 hour to 20 hours, preferably from 2 hours to 10 hours approximately.

The temperatures are in the range of from about 30° C. to about 120° C., preferably from about 60° C. to about 90° C.

The pressure is substantially atmospheric pressure.

It is preferable to operate under a slight nitrogen or inert gas flow. The product (I) so obtained can be separated according to conventional techniques, such as extraction and distillation, after neutralization of the residual basicity in the reaction medium. Otherwise, the raw reaction product as such, containing prevailingly the product (I), can be utilized for the successive reactions of the synthesis process for obtaining "Carbofuran", as described, for example, in the pending application of Stefano Campolmi et al, Ser. No. 234,842 filed Mar. 30, 1981 (assigned to Montedison, S.p.A.) and relating to a two-step process leading to the obtainment of "Carbofuran" starting from the mono-methallyl ether of pyrocatechin, which is heated to 150°–200° C. in a high-boiling neutral organic solvent and then cycled in the presence of acid catalysts.

The present process, according to an effective embodiment, is conducted as follows:

The pyrocatechin, the selected solvent, the selected organic or inorganic base, and the methallyl halide are introduced, in any order, into a thermoregulated reactor equipped with an agitator, a thermometer, a gas bubbler, a reflux cooler and a feeding system for reagents.

Heating of the resulting reaction mixture begins under a continuous slight nitrogen flow until the desired operating temperature is reached, such temperature value being maintained as long as necessary.

At the end of the reaction the resulting product can be separated according to known techniques, which will be described more in detail in the examples; successively, if necessary, the product is quantified according to conventional analytical techniques, such as gas-liquid chromatography and the like.

As an alternative, the raw mono-methallyl ether of pyrocatechin can be directly subjected to the treatments of the art, and in particular those described in the above-cited Campolmi et al application until "Carbofuran" is obtained.

Due to the mild and simple operating conditions, and to the selectivity in the product to be obtained, the present process is particularly advantageous and economical.

The following examples are given to describe the process in more detail, are illustrative, and are not intended to be limiting.

Example 16 was conducted until "Carbofuran" was obtained.

EXAMPLE 1

12 g of sodium carbonate, 11 g of pyrocatechin, 100 cc of 95% ethanol and 20 cc of methallyl chloride were introduced into a thermoregulated 250-cc flask, equipped with a magnetic stirrer, a reflux cooler, a thermometer, a gas bubbler and a feeding system for reagents. Under a slight nitrogen flow the system was heated at reflux (about 70° C.) and was maintained at that temperature for about 5 hours.

At the conclusion of the reaction, the reaction mass was acidified with H$_2$SO$_4$ at 10% and extracted with three portions of 100 cc each of ethyl ether.

The ethereal extract, after dilution to volume, was subjected to gas-chromatographic analysis. Such analysis revealed the presence of 11.6 g of mono-methallyl ether of pyrocatechin (I), corresponding to a yield of 71% referred to the starting pyrocatechin. The monoether (I)/diether (IV) molar ratio was equal to 3.6.

EXAMPLE 2

Utilizing the apparatus described in Example 1, 11 g of pyrocatechin, 16.8 g of sodium bicarbonate, 80 cc of anhydrous ethanol and 20 cc of methallyl chloride were introduced into the reactor.

After 7 hours at about 70° C., the gas-chromatographic analysis of the reaction mixture, separated as in Example 1, revealed that 11.5 g of monoether (I) had formed, with a yield of 70.3% referred to the starting pyrocatechin. The monoether/diether molar ratio was 9.7.

EXAMPLE 3

Into the apparatus as described in Example 1, there were charged 11 g of pyrocatechin, 10.6 g of sodium carbonate, 80 cc of methyl "Cellosolve", and 20 cc of methyallyl chloride. After 3 hours at about 90° C., 13.3 g of monoether (yield referred to the starting pyrocatechin = 81.1%) were obtained, the monoether/diether ratio being of 8.2.

EXAMPLES 4–15

Utilizing the apparatus described in Example 1 and varying the operating conditions, the solvent and the basic system, the results recorded in the following Table (I) were obtained. The mono- and diether yields are molar yields calculated on the starting pyrocatechin. Analogously, the mono-/diether ratio was calculated by moles. In all the examples, 0.1 mole of pyrocatechin in 80 cc of solvent was employed.

TABLE I

| Example | Solvent | Base [moles] | Methallyl chloride [moles] | Temperature [°C.] | Time [h] | Mono [%] | Di [%] | Mono/Di Ratio |
|---|---|---|---|---|---|---|---|---|
| 4 | Anhydrous ethanol | Na$_2$CO$_3$ [0.1] | 20 cc [0.2] | 75 | 7 | 54 | 3 | 18 |

TABLE I-continued

| Example | Solvent | Base [moles] | Methallyl chloride [moles] | Temperature [°C.] | Time [h] | Mono [%] | Di [%] | Mono/Di Ratio |
|---|---|---|---|---|---|---|---|---|
| 5 | Methyl "Cellosolve" | NaHCO₃ [0.2] | 20 cc [0.2] | 90 | 4 | 77.8 | 7.9 | 9.8 |
| 6 | Anhydrous ethanol | TMG [0.12] | 20 cc [0.2] | 75 | 4 | 64.7 | 20.8 | 3.1 |
| 7 | Methanol | NaHCO₃ [0.2] | 20 cc [0.2] | 65 | 7 | 54.6 | 28.8 | 1.9 |
| 8 | H₂O | NaHCO₃ [0.2] | 20 cc [0.2] | 55 | 7 | 21 | 1.2 | 17.5 |
| 9 | H₂O/Ethanol 1:1 | Na₂CO₃ [0.11] | 15 cc [0.15] | 70 | 2 | 54.9 | 8 | 6.8 |
| 10 | H₂O/Methanol 1:1 | Na₂CO₃ [0.11] | 15 cc [0.15] | 65 | 2 | 45.4 | 5.8 | 7.8 |
| 11 | Ethyl "Cellosolve" | Na₂CO₃ [0.11] | 15 cc [0.15] | 90 | 77.1 | 5.5 | 14.0 | |
| 12 | Ethanol at 95% | NaHCO₃ [0.2] | 20 cc [0.2] | 70 | 7 | 65.8 | 19.5 | 3.4 |
| 13 | Methyl "Cellosolve" | K₂CO₃ [0.1] | 20 cc [0.2] | 90 | 3 | 78.8 | 16.4 | 4.8 |
| 14 | Diethylene glycol monomethyl ether | K₂CO₃ [0.2] | 20 cc [0.2] | 90 | 2 | 78.7 | 27.8 | 2.8 |
| 15 | Anhydrous ethanol | NaOH [0.11] | 20 cc [0.2] | 75 | 2 | 55.3 | 16.0 | 3.3 |

EXAMPLE 16

106 g of sodium carbonate, 110 g of pyrocatechin, 1000 cc of 95% ethanol and 200 cc of methallyl chloride were introduced into a thermoregulated 2000 cc reactor, equipped with a mechanical stirrer, a reflux cooler, a thermometer, a gas bubbler and a feeding system for reagents.

The system was heated at reflux (about 70° C.) and kept at that temperature for about 10 hours.

At the conclusion of the reaction, 300 cc of ortho-dichloro-benzene were added and the excess of methallyl chloride and ethanol at 95% were distilled; 879 g of distillate containing about 66 cc of methallyl chloride were collected. After cooling, 500 cc of 10% H₂SO₄ were gradually introduced into the reactor.

The two phases were separated and the aqueous phase was extracted again with 200 cc of ortho-dichlorobenzene. The organic solution of ortho-dichlorobenzene was transferred into a 1000 cc reactor and heated at reflux (about 180° C.) under a nitrogen flow. It was maintained at such temperature for 2 hours, then cooled down to 40° C. and 2 g of paratoluene-sulphonic acid were charged. The mixture was heated at 60° C. for further 2 hours, always under a nitrogen flow. Successively, 1 g of sodium bicarbonate was introduced, with continued stirring for a further 30 minutes.

There were distilled first ortho-dichlorobenzene, which passed at 60°-70° C. at about 10 mm Hg vacuum, then the desired product which passed at 90°-125° C. at 0.8 mm Hg vacuum.

The two fractions were united and extracted, under a nitrogen flow, with three portions of 5% NaOH of 33 cc each. The aqueous phase was then acidified with 10% H₂SO₄ and extracted again with three portions of 300 cc each of methylene chloride.

The organic extract, after drying on sodium sulphate, was transferred into a 1000 cc flask and treated with 30 cc of methylisocyanate and 1 cc of triethylamine. The whole was maintained at 30° C. for about 1 hour, whereupon the solvent was evaporated under a slight vacuum. 94 g of raw "Carbofuran" were obtained. Titer = 85.4%. Yield referred to the starting pyrocatechin = 36.3%.

What is claimed is:

1. A process for preparing the mono-methallyl ether of pyrocatechin of formula (I)

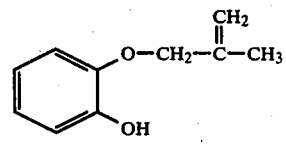

characterized in that pyrocatechin is reacted with a methallyl halide in a homogeneous hydroxylated dissolving medium selected from the group consisting of water, $C_1$–$C_5$ saturated and unsaturated aliphatic monoalcohols, and alcohols having the formula: $RO[(CH_2)_nO]_mH$, wherein R is selected from the group consisting of hydrogen and $C_1$–$C_{10}$ alkyl groups and m and n are integers from 1 to 10, with the proviso that n is at least 2, or mixtures thereof, in the presence of an organic or inorganic base, and at temperatures in the range from about 30° to about 120° C.

2. The process of claim 1, in which the methallyl halide is methallyl chloride.

3. The process of claim 1, in which the solvent is selected from the group consisting of ethyl alcohol, ethylene glycol, allyl alcohol and methyl- or ethyl "Cellosolve" and mixtures thereof.

4. The process of claim 1, in which the base is an inorganic base and is selected from the group consisting of the oxides, hydroxides, carbonates, bicarbonates, and acid phosphates of the alkaline metals.

5. The process of claim 4, in which the inorganic base is selected from the group consisting of sodium and potassium carbonates and bicarbonates.

6. The process of claim 1, in which the base is an organic base and is selected from the group consisting of the tertiary amines of formula $N(R')_3$ in which $(R')_3$ is a homogeneous or heterogeneous hydrocarbyl group.

7. The process of claim 6, in which the base is triethylamine.

8. The process of claim 6, in which the base is tetramethylguanidine.

9. The process of claim 1, in which the weight ratio between the pyrocatechin and the dissolving medium is from about 1:5 to about 1:30.

10. The process of claim 9, in which the weight ratio between the pyrocatechin and the dissolving medium is from about 1:10 to about 1:50.

11. The process of claim 1, in which the molar ratio between the pyrocatechin and the organic or inorganic base is from about 1:0.5 to about 1:3.

12. The process of claim 11, in which the molar ratio between the pyrocatechin and organic or inorganic base is from about 1:1 to about 1:1.5.

13. The process of claim 1, in which the molar ratio between the pyrocatechin and the methallyl halide is from about 1:0.5 to about 1:3.

14. The process of claim 13, in which the molar ratio between the pyrocatechin and methallyl halide is from about 1:1 to 1:1.5.

15. The process of claim 1, in which the reaction is carried out at a temperature from about 60° to about 90° C.

16. The process of claim 1, in which the reaction is conducted in an inert atomsphere.

17. The process of claim 16, in which the reaction is conducted in a nitrogen atmosphere.

* * * * *